United States Patent [19]
Herrmann et al.

[11] Patent Number: 5,515,415
[45] Date of Patent: May 7, 1996

[54] MEDICAL APPARATUS PERMITTING UNIMPEDED PATIENT ACCESS TO THE PATIENT SUPPORT TABLE

[75] Inventors: Klaus Herrmann, Nuremberg; Guenther Krauss, Erlangen; Peter Noegel, Effeltrich, all of Germany

[73] Assignee: Siemens Aktiengesellschaft, Munich, Germany

[21] Appl. No.: 266,247

[22] Filed: Jun. 27, 1994

[30] Foreign Application Priority Data

Jul. 27, 1993 [DE] Germany .............. 43 25 212.5

[51] Int. Cl.⁶ .................................... A61B 6/04
[52] U.S. Cl. .................................. 378/196; 378/195
[58] Field of Search .................. 378/193, 195, 378/196, 197, 198, 208, 209, 177, 8, 95, 65; 5/601; 601/3, 4

[56] References Cited

U.S. PATENT DOCUMENTS

| | | | |
|---|---|---|---|
| 3,322,950 | 5/1967 | Bailey et al. | 378/65 |
| 4,635,284 | 1/1987 | Christiansen | 378/197 |
| 4,674,505 | 6/1987 | Pauli et al. | 128/328 |
| 4,716,581 | 12/1987 | Barod | 378/198 |
| 4,796,613 | 1/1989 | Heumann et al. | 378/196 X |
| 4,887,287 | 12/1989 | Cobben | 378/198 |
| 4,912,754 | 3/1990 | Van Steenberg | 378/196 X |
| 5,014,292 | 5/1991 | Siczek et al. | 378/196 |
| 5,040,203 | 8/1991 | Janssen et al. | 378/196 X |
| 5,044,354 | 9/1991 | Goldhorn et al. | 378/196 X |
| 5,133,338 | 7/1992 | Wess et al. | 378/197 X |
| 5,259,011 | 11/1993 | Petro | 378/20 X |
| 5,329,567 | 7/1994 | Ikebe | 378/65 X |

FOREIGN PATENT DOCUMENTS 9304457.7 U   7/1993   Germany .............. G03B 42/02

*Primary Examiner*—David P. Porta
*Attorney, Agent, or Firm*—Hill, Steadman & Simpson

[57] ABSTRACT

A medical apparatus has a patient support table with a seating surface and a mounting side, the apparatus having at least one apparatus part. At least one of the apparatus part or the patient support table (or the seating surface thereof) is adjustable relative to the other so that the apparatus part and the patient support table assume a mounting position wherein those regions of the apparatus part that have a distance of less than 100 cm from the seating surface measured in vertical direction, are spaced from the edge of the patient support table that limits the mounting side no closer than 40 cm measured horizontally and transversely relative to the edge.

21 Claims, 3 Drawing Sheets

MEDICAL APPARATUS PERMITTING UNIMPEDED PATIENT ACCESS TO THE PATIENT SUPPORT TABLE

BACKGROUND OF THE INVENTION

1. Field of the Invention

The present invention is directed to a medical apparatus of the type having a patient support table with a seating surface and a mounting side and having an apparatus part, wherein the apparatus part and the patient support table are adjustable relative to one another.

2. Description of the Prior Art

In medical examination or treatment systems of the type generally described above, the mounting side can fundamentally be any desired side of the patient support table (having optimally good accessibility), but the mounting side in many instances will be a long side of the patient support table.

In such medical apparatuses, for example, x-ray diagnostics installations or acoustic therapy apparatuses, such as lithotripters, the problem arises that the apparatus part represents an impediment when the patient wishes to mount the seating surface proceeding from the mounting side, or is to be placed on the seating surface by the medical personnel proceeding from the mounting side. This is even true when the possibility exists of lowering and horizontally adjusting the patient support table in the way disclosed by German Utility Model 93 04 457.

SUMMARY OF THE INVENTION

An object of the present invention is to provide a medical apparatus of the type initially described wherein the patient can proceed onto or can be placed on, the seating surface without impediment.

This object is achieved by a medical apparatus constructed in accordance with the principles of the present invention having a patient support table with a seating surface and a mounting side, and having at least one apparatus part, wherein at least one of the apparatus part or the patient support table (i.e., its seating surface) is adjustable relative to the other such that the apparatus part and the patient support table assume a mounting position wherein those regions of the apparatus part that have a spacing of less than 100 cm from the seating surface, as measured in the vertical direction, are spaced from that edge of the patient support table limiting the mounting side no closer than 40 cm, horizontally and transversely from that edge. It is thus assured in the medical apparatus of the invention that the apparatus part cannot represent an impediment when the apparatus part and the patient support table are in their mounting position relative to one another, regardless of whether the patient mounts the seating surface under his or her own power, or is placed on the seating surface by medical personnel.

Only the apparatus part may be made adjustable relative to the patient support table, or only the patient support table may be made adjustable relative to the apparatus part in order to realize the above-described mounting position. It is especially advantageous, however, when both the apparatus part and the patient support table are adjustable relative to one another in a version of the invention in order to realize the mounting position. In this case, the range of adjustment for the apparatus part, or for the patient support table is smaller than when adjusting only one of these components, with the advantage that a slight expansion of the adjustment paths within the adjustment possibilities which are already required for other purposes is adequate under certain circumstances in order to be able to realize the mounting position.

When the apparatus part is attached to a C-shaped arm, in a further version of the invention this C-shaped arm can be displaced away from the mounting side before the mounting position is reached and/or is adjustable along its circumference.

The apparatus part can be a component of an x-ray diagnostics installation, particularly an x-ray radiator, an x-ray image intensifier or a carrier for a component of the x-ray diagnostics installation.

The medical apparatus, however, can have more than one apparatus part displaceable relative to the patient support table in the way set forth.

When the medical apparatus is an apparatus which includes a therapy unit, in an embodiment of the invention the therapy unit is adjustable into a standby position when the apparatus part and the patient support table assume the mounting position, and the regions of the therapy unit located above the seating surface have a spacing measured horizontally and transversely from the edge of the patient support table limiting the mounting side that is not less than 40 cm. It is then assured that neither the apparatus part nor the therapy unit can represent an impediment.

DESCRIPTION OF THE PREFERRED EMBODIMENTS

Figure 1:
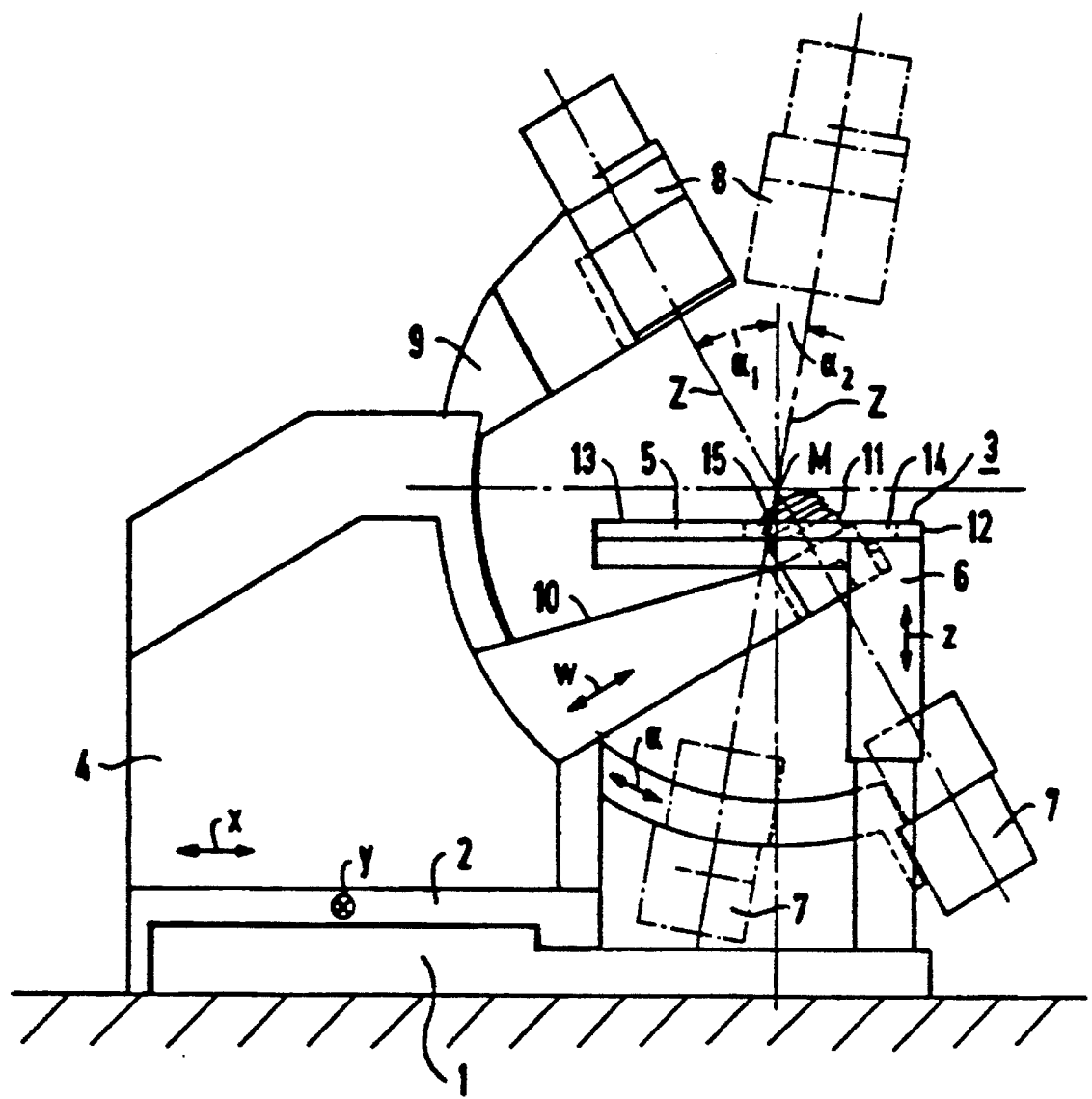
FIG. 1 is a schematic illustration of the apparatus of the invention shown in an end view in a first operating condition.

The apparatus of the invention has a base 1 on which a carriage 2 is adjustable in a direction y proceeding perpendicularly relative to the plane of the drawing, and thus parallel to the longitudinal axis of a patient support table 3. A carrier part 4 is attached on the carriage 2 so as to be longitudinally displaceable in a direction x which proceeds transversely relative to the direction y, and thus transversely relative to the longitudinal axis of the patient support table 3. The support plate 5 of the patient support table 3 is height-adjustable in the z-direction. To this end, the patient support table 3 has two telescoping columns 6 arranged at a distance from one another along the longitudinal direction of the patient support table 3.

An x-ray locating system is attached to the carrier part 4. This x-ray locating system includes an x-ray radiator 7 and an x-ray image intensifier 8 that are attached to the ends of a C-arm 9 lying opposite one another.

The C-arm 9 is connected to the carrier part 4, in a known way not shown in detail so that it can be adjusted in the direction of the curved, double arrow α along its circumference around its middle axis M. The possibility thus exists of irradiating a patient seated on the patient support table 3 from different directions. In FIG. 1, the x-ray locating system is in its first irradiation direction wherein the central ray Z of the x-ray locating system describes the angle $\alpha_1$ with the vertical. The position of the C-arm 9 is indicated with dashed lines for the second irradiation direction, wherein the central ray Z describes the angle $\alpha_2$ with the vertical.

A therapy unit, namely a source 11 of focused acoustic waves, is also attached to the carrier part 4 with a holder 10. This source 11 can be adjusted in the direction referenced w by adjusting the holder 10, from a working position shown in FIG. 1 wherein it projects through a clearance 14 of the support plate 5 relative to the carrier part 4, into a standby position shown in FIG. 2. The source 11 has a flexible application bellows 15 with which it presses against the body surface of the patient for acoustic coupling during treatment.

For implementation of a treatment, the region to be treated is positioned into the active zone of the source 11 assuming its working position. This positioning takes place on the basis of the information acquired with the x-ray locating system by irradiation from the different irradiation directions. This occurs on the basis of a suitable adjustment of the carriage 2 in the y-direction, the carrier part 4 in the x-direction and the support plate 5 in the z-direction.

The source 11, for example, can be an electromagnetic pressure pulse source emitting focused shockwaves as set forth in greater detail, for example, in U.S. Pat. No. 4,674,505.

As may be seen from FIG. 1, two apparatus parts, namely the x-ray image intensifier 8 and the source 11, represent an impediment when the patient wishes to mount the support plate 5, or is to be placed thereon. In the case of the described apparatus, both the mounting of the support plate 5 by the patient and the placing of the patient on the support plate ensue from the long side of the support plate 5 facing away from the carrier part 4, referenced below as the mounting side 12.

As can be seen the x-ray image intensifier 8 is disturbing because it is located relatively closely above the seating surface 13 of the support plate 5. The source 11 represents an impediment because it projects upwardly beyond the seating surface 13 in its working position.

In the apparatus of the invention, the patient support table 3 or the support plate 5 thereof, and the aforementioned apparatus parts, namely the x-ray image intensifier 8 and the source 11, can be adjusted relative to one another so that they assume a mounting position. The regions of the apparatus parts, i.e. of the x-ray image intensifier 8 and of the source 11, that are located above the seating surface 13 in this mounting position have respective spacings a and b of less than 100 cm therefrom measured in the vertical direction. These apparatus parts in this mounting position also have respective spacings c and d that are not less 40 cm, measured horizontally and transversely from that longitudinal edge of the patient support table 3 (i.e., of the patient support plate 5) that limits the mounting side 12.

Figure 2:
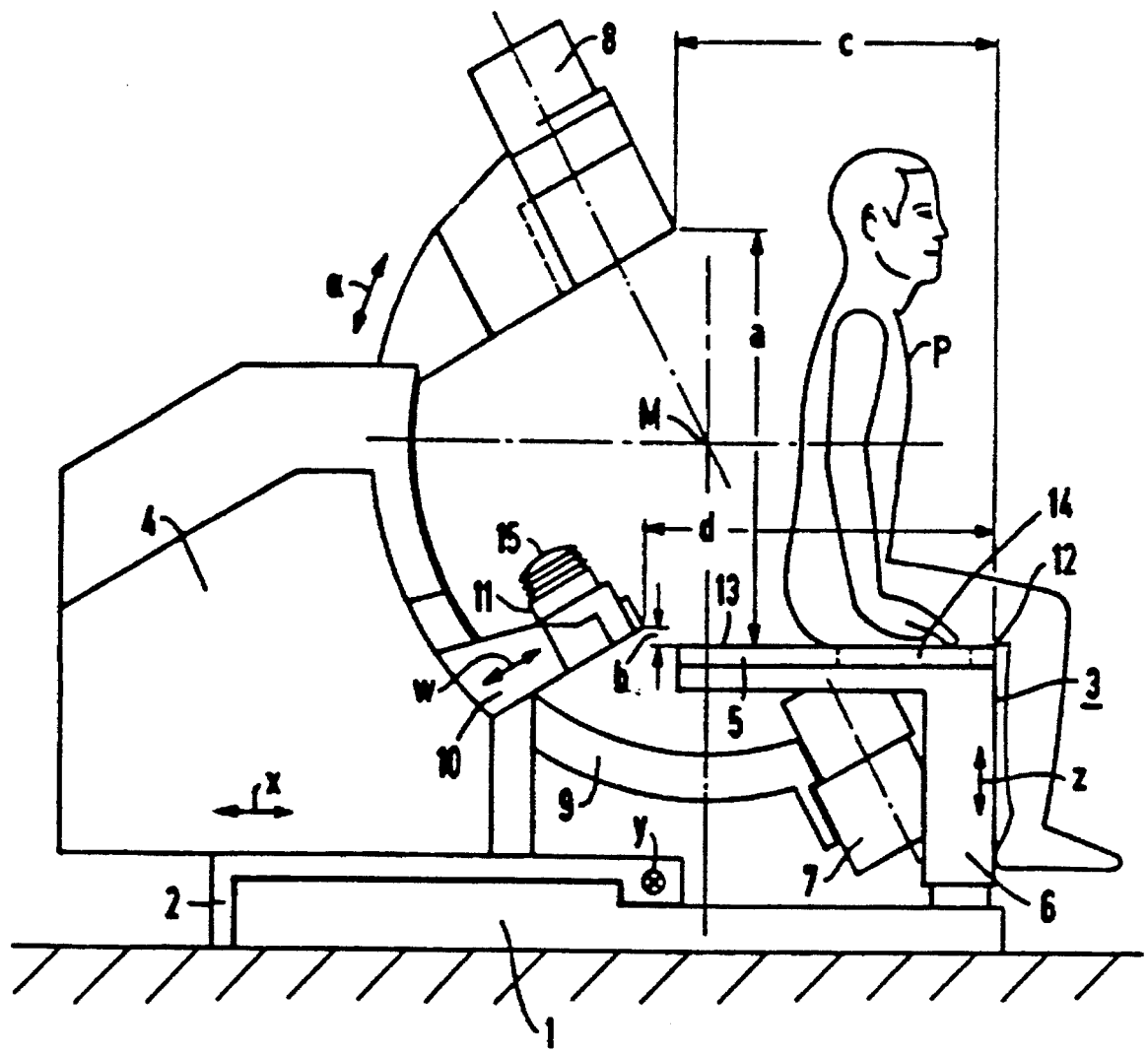
FIG. 2 shows a second operating condition in an illustration analogous to that of FIG. 1.
Figure 3:
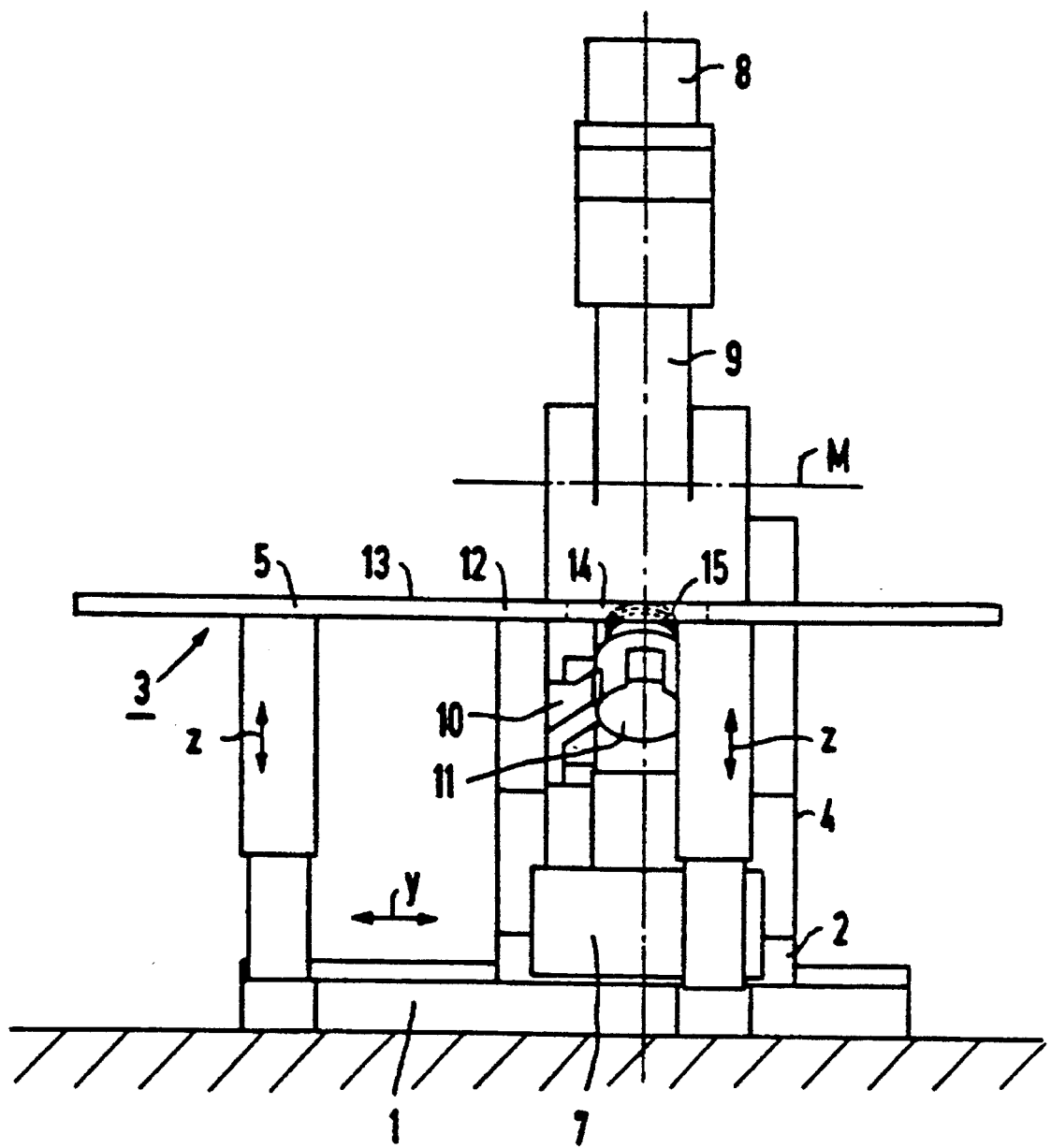
FIG. 3 a side view of the therapy apparatus of the invention.

This position is achieved, according to FIG. 2, in that, first, the carrier part 4 is adjusted in the x-direction away from the patient support table 3, preferably by the maximally possible dimension, and the source 11 is adjusted in the w-direction, likewise away from the patient support table 3, preferably into its standby position. The bearing plate 5 is adjusted downwardly in the z-direction, preferably into its lowest position. The C-bend 9 is adjusted in the $\alpha$ direction so that an enlarged, preferably the maximally possible, distance of the x-ray image intensifier 8 from the mounting side 12 arises.

As is clear with reference to FIG. 2—which shows a patient P when mounting the bearing plate 5 just assuming a sitting position—neither the x-ray image intensifier 8 nor the source 11 can represent an impediment. In particular, there is no limitation whatsoever to the freedom of the head due to the x-ray image intensifier 8.

It is also clear with reference to FIG. 2 that it is possible to place a patient on the patient support plate 5 without any impediment due to the x-ray image intensifier 8 or due to the source 11.

When the patient assumes a supine position on the seating surface 13, wherein that region of the body surface via which the acoustic waves are to be coupled into the patient is located in the region of the clearance 14, the patient support plate 5 is first brought into its uppermost position in the z-direction. Subsequently, the source 11 is brought into its working position in the w-direction. The region to be respectively treated can now be located and be brought into the effective zone of the acoustic waves emanating from the source 11 and can be treated therewith.

After the end of the treatment, the mounting position shown in FIG. 2 is realized again, this time in order to make it possible for the patient P to leave the patient support plate 5 without impediment due to the aforementioned apparatus components, or to be able to comfortably remove the patient from the patient support plate 5.

As a consequence of the fact that the patient support plate 5 is lowered in the mounting position, mounting the patient support plate is further facilitated for the patient, as is the placement of the patient in the support plate 5 by attending personnel, for example transferring the patient from a bed onto the support plate 5.

It is especially advantageous in the case of the described apparatus that adjustment possibilities of the apparatus that are already present can be utilized with modification for the realization of the mounting position.

Although modifications and changes may be suggested by those skilled in the art, it is the intention of the inventors to embody within the patent warranted hereon all changes and modifications as reasonably and properly come within the scope of their contribution to the art.

We claim as our invention:

1. A medical apparatus comprising:

a base;

a patient support table mounted on said base having a patient seating surface and a patient mounting side limited by an edge;

at least one apparatus part mounted on said base;

means for positionally adjusting at least one of said seating surface and said apparatus part relative to the other for causing said seating surface and said apparatus part to assume a mounting position wherein regions of said apparatus part having a distance of less than 100 cm from said seating surface, measured in a vertical direction, are spaced no less than 40 cm horizontally and transversely from said edge, measured from said edge;

a therapy unit mounted on said base for administering therapy to said patient; and means for adjusting said therapy unit into a standby position when said apparatus part and said seating surface assume said mounting position, said therapy unit in said standby position having regions located above said seating surface and said regions being spaced horizontally and transversely from said edge by a distance no less than 40 cm.

2. A medical apparatus as claimed in claim 1 wherein said means for positionally adjusting comprises means for positionally adjusting both said seating surface and said apparatus part into said mounting position.

3. A medical apparatus as claimed in claim 2 wherein said means for positionally adjusting comprises means for positionally adjusting both said seating surface and said apparatus part from an initial position into said mounting position with said spacing of said apparatus part horizontally and transversely from said edge increasing from said initial position to said mounting position.

4. A medical apparatus as claimed in claim 3 wherein said means for positionally adjusting comprises means for adjusting said apparatus part vertically.

5. A medical apparatus as claimed in claim 1 wherein said means for positionally adjusting comprises means for adjusting said seating surface vertically.

6. A medical apparatus as claimed in claim 5 wherein said means for positionally adjusting comprises means for positionally adjusting said seating surface and said apparatus part from an initial position into said mounting position with said spacing of said apparatus part horizontally and transversely from said edge increasing from said initial position to said mounting position.

7. A medical apparatus as claimed in claim 6 wherein said means for positionally adjusting comprises means for adjusting said apparatus part vertically.

8. A medical apparatus as claimed in claim 1 further comprising a C-arm on which said apparatus part is mounted, and wherein said means for positionally adjusting comprises means for shifting said C-arm away from said mounting side.

9. A medical apparatus as claimed in claim 1 further comprising a C-arm on which said apparatus part is mounted, said C-arm having a circumference, and wherein said means for positionally adjusting comprises means for adjusting said C-arm along said circumference.

10. A medical apparatus as claimed in claim 1 further comprising an x-ray diagnostics system having a plurality of components including an x-ray radiator, an x-ray image intensifier, and a carrier for at least one of said x-ray radiator and said x-ray image intensifier, and wherein said apparatus part comprises one of said components of said x-ray diagnostics system.

11. A method for operating a medical apparatus comprising the steps of:

providing a patient support table having a patient seating surface and a patient mounting side limited by an edge;

mounting said patient support table and at least one apparatus part on a common base; and positionally adjusting at least one of said seating surface and said apparatus part relative to the other and thereby bringing said seating surface and said apparatus part to a mounting position and causing regions of said apparatus part having a distance of less than 100 cm from said seating surface, measured in a vertical direction, to be spaced in said mounting position no less than 40 cm horizontally and transversely from said edge, measured from said edge.

12. A method as claimed in claim 11 comprising the future steps of mounting a therapy unit on said base for administering therapy to a patient, adjusting said therapy into a standby position when said apparatus part and said seating surface assume said mounting position, causing said therapy unit in said standby position to have regions located above said seating surface, and causing said regions to be spaced horizontally and transversely from said edge by a distance no less than 40 cm.

13. A method as claimed in claim 11 wherein the step of positionally adjusting comprises positionally adjusting both said seating surface and said apparatus part into said mounting position.

14. A method as claimed in claim 13 wherein the step of positionally adjusting comprises positionally adjusting both said seating surface and said apparatus part from an initial position into said mounting position with said spacing of said apparatus part horizontally and transversely from said edge increasing from said initial position to said mounting position.

15. A method as claimed in claim 14 wherein the step of positionally adjusting comprises means for adjusting said apparatus part vertically.

16. A method as claimed in claim 11 wherein the step of positionally adjusting comprises adjusting said seating surface vertically.

17. A method as claimed in claim 16 wherein the step of positionally adjusting comprises positionally adjusting said seating surface and said apparatus part from an initial position into said mounting position with said spacing of said apparatus part horizontally and transversely from said edge increasing from said initial position to said mounting position.

18. A method as claimed in claim 17 wherein the step of positionally adjusting comprises adjusting said apparatus part vertically.

19. A method as claimed in claim 11 wherein the step of mounting said apparatus part on said base includes carrying said apparatus part on a C-arm mounted on said base, and wherein the step of positionally adjusting comprises shifting said C-arm away from said mounting side.

20. A method as claimed in claim 11 wherein said C-arm has a circumference, and wherein the step of positionally adjusting comprises adjusting said C-arm along said circumference.

21. A method as claimed in claim 11 wherein the step of mounting said apparatus part on said base comprises mounting an x-ray diagnostics system on said base having a plurality of components including an x-ray radiator, an x-ray image intensifier, and a carrier for at least one of said x-ray radiator and said x-ray image intensifier, with said apparatus part comprising one of said components of said x-ray diagnostics system.

* * * * *